United States Patent [19]

Apffel, Jr. et al.

[11] Patent Number: 4,784,962

[45] Date of Patent: Nov. 15, 1988

[54] MIXTURE OF AMINO ACID DERIVATIVES, PROCESS OF PRODUCING THE MIXTURE AND USE OF THE MIXTURE FOR QUANTITATIVE DETERMINATION OF THE AMINO ACIDS

[75] Inventors: James A. Apffel, Jr., Los Gatos, Calif.; Rainer Schuster, Marxzell-Burbach, Fed. Rep. of Germany

[73] Assignee: Hewlett-Packard Company, Palo Alto, Calif.

[21] Appl. No.: 18,890

[22] Filed: Feb. 25, 1987

[30] Foreign Application Priority Data

Feb. 26, 1986 [EP] European Pat. Off. ........... 86102505

[51] Int. Cl.$^4$ ...................... G01N 21/77; G01N 33/68
[52] U.S. Cl. ..................................... 436/89; 436/111; 436/161; 436/172
[58] Field of Search ................... 436/89, 90, 111, 161, 436/172, 174

[56] References Cited

U.S. PATENT DOCUMENTS

| | | | |
|---|---|---|---|
| 3,531,490 | 9/1970 | Friedman et al. | 436/89 |
| 4,021,198 | 5/1977 | Fujita et al. | 436/90 |
| 4,133,753 | 1/1979 | Takeuchi et al. | 436/89 |
| 4,670,403 | 6/1987 | Ishida et al. | 436/89 |

FOREIGN PATENT DOCUMENTS

| | | | |
|---|---|---|---|
| 0183950 | 6/1986 | European Pat. Off. | |
| 2622547 | 11/1977 | Fed. Rep. of Germany | 436/89 |
| 143030 | 1/1961 | U.S.S.R. | 436/111 |

OTHER PUBLICATIONS

Fluorometric Determination of Thiols by Liquid Chromatography With Post Column Derivatization, Nakamura et al., Analytical Chemistry, vol. 53, No. 14, Dec. 81.
Kang S. Lee et al., Derivatization of Cysteine and Cystine for Fluorescence Amino Acid Analysis with the O-Phthaldialdehyde/2-Meicaptoethanol Reagent, Journal of Biological Chemistry, vol. 254, No. 14, Jul. 1979, pp. 6248-6251.
S. Simons, Jr. et al., Reaction of O-Phthalodehyde and Thiols With Primary Amines; Formation of 1-Alkyl (and Aryl) Thio-$\alpha$-Akylisoindoles, J. Org. Chem., vol. 43, No. 14, 1978, pp. 2886-2896.
Chromatography of Amino Acids on Sulfonated Polystyrene Resins, vol. 30, No. 7, Analytical Chemistry: pp. 1185-1189, Stanford Moore et al., Jul. 1958.
Amino Acid Analysis by Reverse-Phase High-Performance Liquid Chromatography: Precolumn Derivatization with Phenylisothiocyanate (Analytical Biochemistry) pp. 65-74, Robert Heinrikson et al., 1984.
High Performance Liquid Chromatographic Determination of Subpicomole Amounts of Amino Acids by Precolumn Fluorescence Derivatization with O-Phthaldialdehyde Analytical Chemistry, vol. 51, No. 11, Peter Lindroth et al., 1979.
Determination of Amino Acids with 9-Fluorenylmethyl Chloroformate and Reversed-Phase High-Performance Liquid Chromatography, Journal of Chromatography, S. Einarsson et al., pp. 609-618, 1983.
Dansylation of Amino Acids for High-Performance Liquid Chromatography Analysis; Analytical Biochemistry, Yitzhak Tapuhi et al., pp. 123-129, 1981.
Fluorescence Reaction for Amino Acids; Analytical Chemistry, vol. 43, No. 7, Marc Roth, pp. 880-882, Jun. 1971.
Measurement of Free Amino Acids in Human Biological Fluids by High-Performance Liquid Chromatography; Journal of Chromatography, Herbert Codel et al., pp. 49-61, 1984.

*Primary Examiner*—Barry S. Richman
*Assistant Examiner*—Lyle Alfandary-Alexander
*Attorney, Agent, or Firm*—Frank R. Perillo

[57] ABSTRACT

A mixture of fluorescently-excitable amino acid derivatives suitable for use in quantitative amino acid analysis is provided in which primary amino acids are present as derivatives of a first reagent and secondary amino acids are present as derivatives of a second different reagent. The process for preparing the mixture comprises the steps of derivatization of the primary amino acids of an amino acid sample with ortho-phthalaldehyde (OPA) and of derivatization of the secondary amino acids of the sample with fluorenylmethylchloroformate (FMOC) in the presence of acetonitrile. The mixture can be obtained automatically and is highly suitable for fast analysis by reversed-phase liquid chromatography.

20 Claims, 1 Drawing Sheet

MIXTURE OF AMINO ACID DERIVATIVES, PROCESS OF PRODUCING THE MIXTURE AND USE OF THE MIXTURE FOR QUANTITATIVE DETERMINATION OF THE AMINO ACIDS

BACKGROUND OF THE INVENTION

The present invention relates to the chemical derivatization of amino acids. More specifically, a method is disclosed for the preparation of fluorescent derivatives of amino acids suitable for analysis and detection using liquid chromatography with reversed phase separation columns. In general the method can be applied to the analysis of amino acids in a variety of matrices such as physiological fluids, pharmaceuticals, foods and beverages, etc.

Today, in many technical areas, the analysis of amino acids is an important requirement. Particularly in the rapidly growing area of biotechnology, this analysis is a critical procedure in the characterization of proteins and peptides. In addition, amino acid analysis is required in the medical field, where characterization of amino acids in biological materials can be useful in diagnostic procedures; in the pharmaceutical field for development and quality control of products; and in the food and beverage area, again for product characterization.

For successful amino acid analysis, typically between 18 and 35 amino acids (depending on the matrix) must be separately quantified in amounts typically between 100 femtomoles ($10^{-13}$ moles) and 1 nanomole ($10^{-9}$ moles) each, preferably with less than 5% sample to sample relative standard deviation, often in the presence of other matrix components, and preferably in less than 1 hour per sample. Modern developments favor high sensitivity and fast analyses.

Most analytical procedures for amino acids are based on liquid chromatography, either in its modern high performance form (HPLC), or as classical medium pressure liquid chromatography. In either case, the major problem in the analysis is the selective and sensitive detection of these compounds. With few exceptions, the amino acids do not show strong optical absorption above 220 nm. This precludes the use of ultraviolet/visible spectrophotometric detection at the required sensitivity. Similarly, detection based on refractive index lacks the required sensitivity. For these reasons, chemical derivatization procedures are generally used. The chemical derivatizations tag the compounds with a chemical group so that the resulting product has strong response for either UV/VIS or Fluorescence detection. The derivatization procedure can be performed prior to the chromatographic separation ("precolumn") or after the separation ("postcolumn").

In most cases, the amino group of the amino acid is used as the active site for the chemical derivatization, but because of the diverse chemical nature and reactivity of the various amino acids, the analysis still is not of uniform exactness. Around a common backbone, the amino acids contain such differing functional groups as aliphatic, aromatic, primary amines, secondary amines, carboxylic acids, amides and thiols. This makes it difficult to find a reagent which will react with all amino acids and yield comparable sensitivity.

Current chromatographic methods for amino acid analysis can be classified on the basis of the derivatization mode (precolumn or postcolumn) or the detection mode (UV/VIS or Fluorescence) (*Amino Acid Analysis*, J. M. Rattenbury ed. (Wiley Interscience, New York, 1981)).

In terms of the derivatization mode, precolumn derivatization is becoming increasingly more popular because it allows the use of high efficiency, small particle, reversed phase chromatographic columns. Postcolumn derivatization can be used only after separation of the amino acids using ion exchange chromatography, which tends to exhibit poorer chromatographic efficiency and longer analysis time.

The most popular UV/VIS derivatization reactions for amino acids employ either ninhydrin (S. Moore, D. H. Spackmann and W. H. Stein, Anal. Chem. 30 (1958) 1185-1205) or PITC (phenylisotHiocyanate) (R. L. Hendrickson and S. C. Meredith, Anal. Bioch., 136 (1984) 65-74). UV/VIS derivatization, however, has relatively low detection sensitivity compared to fluorescence detection. Ninhydrin can be used only postcolumn, but allows the detection of all amino acids. PITC is run precolumn and allows detection of all amino acids, but requires a derivatization procedure which is not amenable to automation.

The most popular fluorescence derivation reactions utilize either OPA (ortho-phthalaldehyde) (P. Lindroth and K. Mopper, Anal. Chem. 51 (1979) 1667 and M. Roth, Anal. Chem. 43/1971) 880); FMOC (Fluorenylmethylchloroformate) (S. Einarsson, B. Josefsson and S. Lagerkvist, J. Chromatogr. 292 (1983) 609-618); or Dansyl Chloride (Y. Tapuhi, D. E. Schmidt, W. Lindner and B. L. Karger, Anal. Bioch. 15 (1981) 123). OPA is based on a simple, fast, easily automated procedure with high sensitivity, but reacts only with primary amines. Current methods usually react OPA in the presence of mercaptoethanol which results in reagent and products with limited stability. Both FMOC and Dansyl Chloride are used precolumn, deliver high sensitivity, and react with primary and secondary amines, but require long reaction times and ancillary procedures, such as extractions, to remove excess reagent.

The simultaneous detections of both cystine and cysteine have presented particular problems in the past for the aforesaid methods. Cystine is a molecule composed of two cysteine molecules joined by a disulfide bridge. Generally, a derivative of either cystine or cysteine can be detected by the prior art, but the substantial interconversion of one to the other that can often take place, depending on the sample history, lowers the accuracy of the analysis for either.

SUMMARY OF THE INVENTION

The present invention provides a mixture containing fluorescent derivatives of both primary and secondary amino acids, optionally with remainders of derivating agents, which can be separated by reversed-phase liquid chromatography in such a way that any primary amino acid derivatives elute from the separating column in a sequence with no interspersed elution of any secondary amino acid derivatives and that substantially no remainder from the derivatization process elutes from the chromatographic column at such time as to impede the quantitative determination of any amino acid derivative by wavelength-selective chromatographic detection.

The present invention also provides a process for producing the mixture described above wherein the sequence of processing steps is adapted to provide a specific difference between the primary amino acid derivatives and the secondary amino acid derivatives. In one step of the process, the primary amino acids are converted to derivatives of ortho-phthalaldeyhde (OPA) and mercaptopropionic acid (MPA) using OPA/MPA dissolved in acetonitrile; in another step, the secondary amino acids are converted to FMOC derivatives using FMOC dissolved in acetonitrile, all in the presence of suitable buffers for pH adjustment.

The invention provides a pathway to amino acid analysis having, in particular, high sensitivity reliable detection of both primary and secondary amino acids total automation capability short analysis time (1 hour total analysis cycle)

Preferred embodiments of the invention provide specific advantages as follows:

(a) Cysteine, which does not form a fluorescent product with OPA/MPA if unmodified, can be modified to form a fluorescent OPA/MPA derivative by blocking its thiol group with an alkyl group. Any cystine contained in an initial mixture of acids can be converted into cysteine by reductive cleaving using a reducing agent having a mercapto functional group and a higher oxidation potential than cysteine. The cysteine thiol group can subsequently be blocked using a strong alkylating agent, so that in the subsequent OPA/MPA derivatization of primary amino acids, the cysteine forms a fluorescent OPA/MPA derivative. Any ambiguity in the detection of cystine/cysteine is thus avoided because all cystine is converted to cysteine prior to the derivatization.

(b) All derivatizing reagents used in the present invention are compatible with subsequent chromatographic analysis, and therefore the need to perform an extraction of substances from the mixture during the processing is obviated. Thus, the entire analytical process can be carried out in the sample drawing unit of a chromatograph. An apparatus such as is disclosed in European Patent Publication No. 0183950A1, published June 11, 1986 is particularly suitable for this purpose.

(c) Complete separation between the derivatives of the primary amino acids and the secondary amino acids of the mixture of this invention can be obtained by reversed-phase liquid chromatography. In such an application, wavelength-specific analysis in which the column elute is irradiated with light specific to the OPA/MPA derivatives followed by a separate irradiation with light specific to FMOC derivatives.

DETAILED DESCRIPTION OF THE INVENTION

Figure 1:
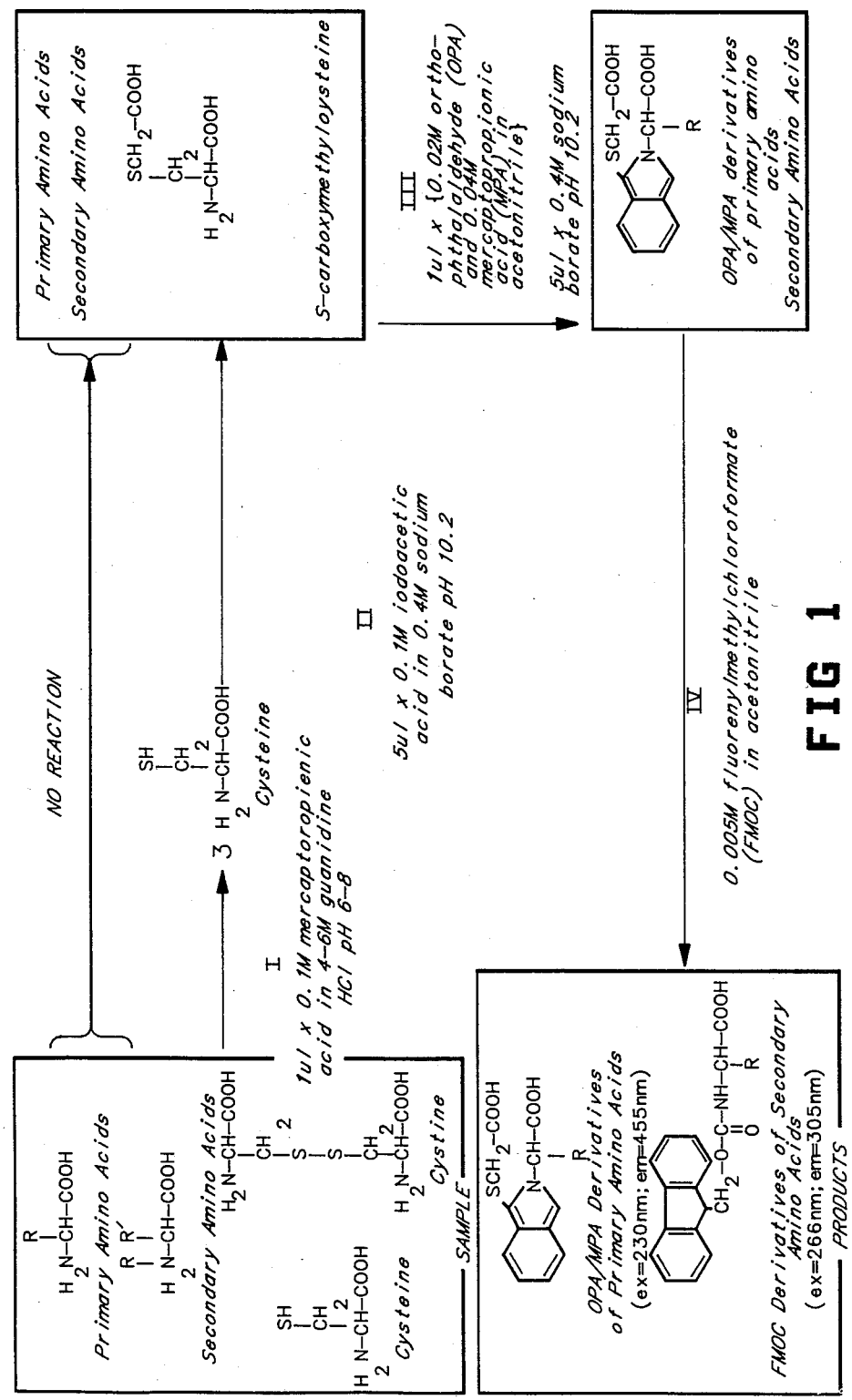
FIG. 1 is a schematic representation of a preferred reaction sequence of the present invention.

According to the present invention, a sample containing at least one primary amino acid and at least one secondary amino acid can be treated to form therefrom a mixture suitable for analysis. The mixture is prepared by treating the sample with a solution of OPA and MPA in acetonitrile to convert any primary amino acids present to OPA/MPA derivatives, followed by treating with a solution of FMOC in acetonitrile to convert any secondary amino acids present to FMOC derivatives. The resultant mixture consists essentially of OPA/MPA derivatives of primary amino acids and FMOC derivatives of secondary amino acids, both of which are capable of fluorescent excitation. Essentially no OPA/MPA derivatives of secondary amino acids or FMOC derivatives of primary amino acids are present. In preferred embodiments, in which the amino acids are treated with excess derivatizing reagents, the mixture further contains unreacted MPA, OPA, and/or FMOC.

Whereas the invention is substantially based on the subsequent and different derivatization of first the primary amino acids and then the secondary amino acids, a preferred embodiment of the process according to the invention can be carried out in a sequence of four reaction steps. Although each reaction step is carried out on the entire analytical sample, not all analytes take part in each reaction. The reaction proceeds as follows:

(I) In a first facultative reaction step, a sample or substrate containing at least one primary and at least one secondary amino acid is mixed with a reductive cleaving agent, preferably mercaptopropionic acid (or dithioerythritol) in urea or guanidine hydrochloride. The effect of this reaction is to transform any cystine present in the sample into cysteine by reductively cleaving the disulfide bridge. This converts the cystine into a form in which a strongly fluorescent product can be formed e.g. with ortho-phthalaldehyde. By converting cystine to cysteine, one reaction can be used to determine the sum quantity of both compounds. Other amino acids that are present in the sample are unaffected in this reaction.

(II) The sample is then treated with an agent to react with the thiols present (i.e. from native cysteine and the cysteine newly converted from cystine in step I). Iodoacetic acid is preferred for this purpose, to form carboxymethylcysteine. The purpose of this reaction is to convert the cysteine into a form which can form a strongly fluorescent product e.g. with ortho-phthalaldehyde. It is reported (M. Roth, Anal. Chem., 43 (1971) 880) that cysteine will not form a fluorescent product with OPA unless the thiol group is blocked. Other amino acids are unaffected by this reaction.

(III) The sample is then treated with a suitable buffer, such as a volume of borate buffer at pH 10.2, to adjust the pH and then with a volume of reagent containing ortho-phthalaldehyde (OPA) and mercaptopropionic acid (MPA) (H. Godel, T. Graser, P. Foldi, P. Pfaender and P. Furst, J. Chromatogr. 297 (1984) 49–61), preferably in acetonitrile. In this reaction all primary amino acids present, including any carboxymethylcysteine from step II, form a fluorescent isoindole product which can be separated by reversed phase liquid chromatography and detected using fluorescence (lambda ex=230 nm, lambda em=455 nm). Any secondary amino acids present in the sample are unaffected by this reaction since OPA only reacts with primary amines. The use of the derivatization reagent dissolved in acetonitrile is a significant improvement since the reagent itself has improved stability in this solution. Previous work has used OPA and MPA (or, more commonly mercaptoethanol) dissolved in borate buffer, which is stable for a maximum of 1-2 weeks.

(IV) Finally the reaction mixture (now containing derivatized primary amino acids, free secondary amino acids and possibly excess reagents) is treated with a solution of fluorenylmethylchloroformate (FMOC), preferably in acetonitrile, to form fluorescent products with the secondary amino acids. The products exhibit fluorescence with lambda excitation=266 nm and lambda emission=305 nm. Although FMOC reacts with primary amines as well, all primary amino groups have been previously blocked in the formation of OPA/MPA derivatives in step III. Any excess reagent FMOC is partially converted to a hydrolysis product resulting in two fluorescent compounds (reagent and hydrolysis product) which can be, but need not be, separated chromatographically from the analytes.

FIG. 1 schematically depicts a particularly preferred procedure for forming the mixture of this invention by the sequential treatment of a sample with OPA and FMOC.

After the reaction procedure has been completed, the product resulting from the original sample (which contained primary amino acids, including cystine and cysteine, and secondary amino acids) is a mixture of OPA derivatives representing the primary amino acids and FMOC derivatives representing the secondary amino acids. The sum of cysteine and cystine are represented by a OPA product of carboxymethylcysteine. This mixture can be separated using gradient elution reversed phase chromatography, preferably using conditions to be described below. The use of two separate chemical derivatives additionally allows an added dimension of selectivity, namely that of spectral selectivity.

For maximum sensitivity, fluorescence detection is the analytical technique preferred for use on the derivatized mixtures, of the invention, but the procedure is also amenable to UV/VIS detection using two simultaneous or sequential detection wavelengths (338 nm for the OPA derivatives, and 266 nm for the FMOC derivatives).

The following is a list of features and advantages of the mixture and the method according to the invention and of preferred embodiments. Wherever possible, advantages in comparison to previously-used systems are indicated.

1. All important amino acids, both primary and secondary, are determined in a single analysis. This is in comparison to the derivatization of amino acids using ortho-phthalaldehyde alone in which only primary amino acids are determined.

2. Cystine and cysteine are determined. Preferably the sum amount of cystine and cysteine is determined as a single chromatographic peak. This is to be compared favorably with methods which determine only cystine or cysteine, in which the interconversion of the two is not taken into account.

3. High Sensitivity. The use of fluorescence derivatization and detection allows detection at amounts as low as 50–100 femtomoles. This detection limit is to be compared with UV/VIS methods which yield detection limits in the low picomole range.

4. High Selectivity via Spectral information. By using two classes of derivatives (OPA and FMOC), a class separation between primary and secondary amino acids can be made based on spectral differences. This can be seen as an extra dimension of selectivity in addition to the chromatographic separation. It simplifies clear differentiation between the two classes of compounds and makes rapid evaluation of chromatographic data easier than methods in which all amino acids are detected under identical conditions.

5. Fast derivatization procedure. As described below, the entire derivatization procedure requires 5–10 minutes.

6. Fast analysis time. The mixtures are amenable to analysis by use of small particle reversed phase chromatographic columns and gradient elution techniques, which are substantially more rapid than another derivatization/analysis systems. Using an automated derivatization procedure, the entire sample cycle can be performed in 35 minutes. This is to be compared with methods using post-column derivatization in which ion-exchange chromatographic is used, requiring 1–1.5 hours per sample. Additionally, reversed phase chromatographic columns tend to be more stable than ion-exchange columns.

7. Room temperature reaction. The derivatization reaction takes place at ambient temperature, thus requiring no additional hardware for thermostatic control. This is to be compared with the phenylisothiocyanate (PITC) method in which a long reaction requires elevated temperatures and a special hardware module for operation.

8. Homogeneous, compatible reagents. All the reagents used in the procedure are mutually compatible, an essential feature of the method. In other words, there is no cross reaction or interference between one reaction and another. Although the individual reaction steps have been described in one form or another, modifications have had to be made to ensure this compatibility. For example, OPA has heretofore typically been dissolved in a borate buffer containing 1–5% methanol, but it has been found that methanol can interfere with the FMOC reaction, so that the OPA solvent was preferably changed to 100% acetonitrile which does not interact with FMOC. The homogeneous character of the reaction (i.e., the entire reaction can be carried out in a single vessel, adding one reagent at a time, with no need to remove reagents) makes the systems ideal for automation. Again this should be compared with the PITC method, in which excess reagent must be removed under vacuum, or the FMOC method, in which the excess reagent is extracted.

9. Easily Automated. The derivatization procedure can be automated using a computer controlled HPLC autosampler system such as that described in the European Patent Publication No. 0183950A1, published June 11, 1986, the disclosure of which is hereby incorporated by reference. It should be noted that although there is advantage in terms of sample throughput and automation capability, the method of the invention is still valid and useful in a manual mode and does not depend on the automation aspect for success or operability.

10. Use of Mercaptopropionic Acid in OPA reaction. The use of mercaptopropionic acid, in place of heretofore used mercaptoethanol, in the OPA reaction causes higher fluorescence yield and results in stable fluorescence products. Mercaptoethanol yields unstable products with halflives measured in minutes.

11. Stable reagent solutions. The preferred use of acetonitrile as a solvent for the ortho-phthalaldehyde/mercaptopropionic acid reagent and for the FMOC reagent provides solutions which have improved stability. This is a very important improvement, because using a buffer as solvent (in the absence of some stabilizer) results in a reagent which is only stable for a matter of weeks. This is a critical point if the reagents are to be prepared in large batches and later sold and distributed.

12. Non-toxic reagents. As opposed to reagents such as nitrobenzooxadiazole chloride (NBD-Cl) or nitrobenzooxadiazole fluoride (NBD-F), the reagents are relatively safe in a hygienic sense.

Following are specific exemplifications of the reaction steps involved in the above procedure. There are provided acceptable ranges for reagent volumes and concentrations shown parenthetically next to the particular values used in the examples. The procedures described assume 1 microliter starting sample volume, although this volume can be varied if corresponding variations are made in the reagent volumes. All reagents used are preferably analytical grade. Thorough mixing takes place after the addition of each reagent.

I. One microliter of sample is mixed with 5 microliters (1-10 microliters) of 0.1M (0.01-0.5M) mercaptopropionic acid dissolved in 4M (3-6M) urea or guanadine hydrochloride at pH 6-8. Alternatively, 0.4M (0.1-0.4M) sodium borate buffer adjusted to pH 10.2 (9.5-10.5) with sodium hydroxide can be used as solvent. In place of mercaptopropionic acid, 0.1M (0.01-0.5M) dithioerythritol can be used. The reaction proceeds at room temperature (20°-30° C.) within 1 to 5 minutes.

II. To the mixture of step I is added 0.1M (0.05-0.3M) iodoacetic acid dissolved in 0.4M (0.1-0.4M) sodium borate buffer adjusted to pH 10.2 (9.5-10.5) with sodium hydroxide. The exact concentration of iodoacetic acid should be approximately as a 10 fold molar excess to the amount of any cysteine expected in the mixture (including that converted from cystine). The reaction proceeds at room temperature in 1 to 5 minutes. In place of iodoacetic acid, iodacetamide can be used, resulting in a different product than carboxymethylcysteine and with different chromatographic properties.

III. To the reaction mixture resulting from step II (or to one microliter of initial sample, assuming the presence of no cysteine or cystine in the initial sample) add 5 microliters (1-10 microliters) of 0.4M (0.1-0.4M) sodium borate buffer adjusted to pH 10.2 (9.5-10.5) and 1 microliter (1-5 microliters) of a solution containing 0.02M (0.01-0.1M) ortho-phthalaldehyde and 0.04M (0.01-0.1M) mercaptopropionic acid dissolved in acetonitrile. The reaction proceeds at room temperature in 1 to 5 minutes.

IV. To the reaction mixture resulting in step III, add 1 microliter (1-5 microliters) of a solution containing 0.01M (0.005-0.05M) fluorenylmethylchloroformate dissolved in acetonitrile. The reaction proceeds at room temperature in 1-5 minutes.

The entire reaction mixture is then injected directly into a High Performance Liquid chromatograph with the following typical, but not limiting, conditions:

Analytical Conditions

Column: 200×2.1 mm i.d. 5 μm Hypersil ODS (octa decylsilane modified silicagel)
Column Temperature: 35° C.
Mobile Phases:
  A: 2.4 g/L sodium acetate, 0.25% tetrahydrofuran, in bidistilled water
  B: 80% acetonitrile, 20% 0.1M sodium acetate in bidistilled water.
Initial flow rate: 0.22 ml/min
Gradient program:
  AT T=0; A=98% B=2%
  AT T=10; A=82% B=18%
  AT T=18; A=71% B=29%
  AT T=20; A=55% B=45%
  AT T=22; A=48% B=52%
  AT T=24; A=00% B=100%
  AT T=29; A=00% B=100%
  AT T=31; A=98% B=2% (times in minutes)

Detection parameters

Fluorescence Detection:
  OPA derivatives (T=0-21 minutes)
    Excitation wavelength=230 nm; band width=5 nm
    Emission wavelength=455 nm; band width=5 nm
  FMOC Derivatives (T=21-25 minutes)
    Excitation wavelength=266 nm; band width=5 n,
    Emission wavelength=305 nm; band width=5 nm
UV/VIS Detection:
  OPA derivatives:
    Signal: 338 nm, Bandwidth: 10 nm
    Reference: 390 nm Bandwidth: 20 nm
  FMOC Derivatives:
    Signal: 266 nm Bandwidth: 4 nm
    Reference: 349 nm Bandwidth: 6 nm These HPLC analytical conditions are given as typical without being limiting.

What is claimed is:

1. A mixture of fluorescently-excitable derivatives of amino acids consisting essentially of OPA/MPA derivatives of primary amino acids and FMOC derivatives of secondary amino acids.

2. The mixture of claim 1 further containing unreacted OPA, MPA, FMOC, or a mixture of these.

3. The mixture of claim 2 further containing acetonitrile.

4. The mixture of claim 1 in which said primary amino acid derivatives comprise at least an OPA/MPA derivative of cysteine wherein the thiol group is blocked.

5. The mixture of claim 4 in which the thiol group is blocked by a methylcarboxy group.

6. The mixture of claim 1, 4, or 5 wherein the mixture is in the form of an aqueous solution, said mixture further containing acetonitrile.

7. A process for preparing a mixture of amino acid derivatives amenable to excitation under fluorescent light comprising the steps of
  (a) providing a sample containing at least one primary amino acid and at least one secondary amino acid;
  (b) treating the sample with a buffer and with a solution of OPA and MPA in acetonitrile, in any sequence, to obtain a first mixture; and
  (c) treating said first mixture with a buffer and with a solution of FMOC in acetonitrile in any sequence.

8. The process of claim 7 wherein the sample contains cystine and wherein the process comprises the additional steps, performed prior to step (b), of (1) treating the sample with a buffer and a reducing agent having a functional mercapto group and a higher oxidation potential than cysteine to convert cystine to cysteine, and (2) treating the resultant sample with a buffer and an alkylating agent to block free thiol groups on any cysteine present.

9. The process of claim 8 in which the alkylating agent is iodoacetic acid or iodoacetamide.

10. The process of claim 8 in which the reducing agent is mercaptopropionic acid and the alkylating agent is iodoacetic acid.

11. The process of claim 8 in which the reducing agent is mercaptopropionic acid or dithioerythrital.

12. The process of claim 8 or 11 comprising the additional step of introducing said sample into a sample drawing unit of a chromatograph prior to any of said treating steps.

13. A process for quantitatively analyzing a sample of amino acids containing at least one primary amino acid and at least one secondary amino acid comprising the steps of (a) providing a sample containing at least one primary amino acid and at least one secondary amino acid;
(b) treating the sample with a buffer and with a solution of OPA and MPA in acetonitrile, in any sequence, to obtain a first mixture;
(c) treating said first mixture with a buffer and with a solution of FMOC in acetonitrile in any sequence to form a second mixture;
(d) introducing at least a portion of the second mixture into a separatory device and eluting primary amino acid derivatives independently of secondary amino acid derivatives to form an eluent with no interspersed elution of primary and secondary amino acid derivatives; and
(e) analyzing the eluent to quantitatively determine the amounts of primary and secondary amino acid and derivatives thereof.

14. The process of claim 13 in which the separatory device is a reversed-phase liquid chromatography column.

15. The process of claim 14 wherein the sample contains cystine and wherein the process comprises the additional steps, performed prior to step (b), of (1) treating the sample with a buffer and a reducing agent having a functional mercapto group and a higher oxidation potential than cysteine to convert cysteine to cysteine, and (2) treating the resultant sample with a buffer and an alkylating agent to block free thiol groups on any cysteine present.

16. The process of claim 15 in which the reducing agent is mercaptopropionic acid or dithioerythrital.

17. The process of claim 15 in which the alkylating agent is iodoacetic acid or iodoacetamide.

18. The process of claim 15 in which the reducing agent is mercaptopropionic acid and the alkylating agent is iodoacetic acid.

19. The process of claim 14 or 15 wherein the analyzing step includes irradiating the eluent during a first period of time with at least a first wavelength of light specific to the excitation of OPA/MPA derivatives of primary amino acids, irradiating the column elute during a second period of time with at least a second wavelength of light specific to excitation of FMOC derivatives of secondary amino acids, and detecting any light emitted from said eluent.

20. The process of claim 14, 15 or 19 in which the column is packed with octadecylsilane-modified silica gel.

* * * * *